United States Patent
Kobayashi et al.

(10) Patent No.: US 8,163,541 B2
(45) Date of Patent: *Apr. 24, 2012

(54) CELL CULTURE APPARATUS AND CONTROL METHOD THEREOF

(75) Inventors: Toyoshige Kobayashi, Hatoyama (JP); Kazutoshi Kan, Kawagoe (JP)

(73) Assignee: Hitachi, Ltd., Tokyo (JP)

( * ) Notice: Subject to any disclaimer, the term of this patent is extended or adjusted under 35 U.S.C. 154(b) by 987 days.

This patent is subject to a terminal disclaimer.

(21) Appl. No.: 11/984,160

(22) Filed: Nov. 14, 2007

(65) Prior Publication Data

US 2008/0145924 A1    Jun. 19, 2008

(30) Foreign Application Priority Data

Dec. 15, 2006    (JP) .................................. 2006-338067

(51) Int. Cl.
*C12M 1/00*    (2006.01)
*C12M 3/00*    (2006.01)

(52) U.S. Cl. ............... 435/303.1; 435/294.1; 435/305.2; 435/305.3; 435/288.3; 435/288.4; 435/307.1

(58) Field of Classification Search ............... 435/303.1, 435/305.2, 305.3, 294.1, 288.3, 288.4, 307.1
See application file for complete search history.

(56) References Cited

U.S. PATENT DOCUMENTS

| | | | |
|---|---|---|---|
| 5,534,227 | A | 7/1996 | Lahm et al. |
| 2003/0223907 | A1 | 12/2003 | Schmelz et al. |
| 2006/0115893 | A1 | 6/2006 | Kobayashi et al. |

FOREIGN PATENT DOCUMENTS

| | | |
|---|---|---|
| EP | 0 688 602 A2 | 2/1995 |
| EP | 0 688 602 A3 | 2/1995 |
| JP | 1-225476 | 3/1988 |
| JP | 2004-089126 | 9/2002 |
| JP | 2005-287466 A | 4/2004 |
| JP | 2006-149237 | 11/2004 |
| WO | WO 96/21855 | 1/1996 |
| WO | WO 01/91895 A1 | 5/2001 |

OTHER PUBLICATIONS

Partial European search report (R. 64 EPC) for European Application No. 07022235.1-1521, dated Apr. 25, 2008.

*Primary Examiner* — Nathan Bowers
*Assistant Examiner* — Gautam Prakash
(74) *Attorney, Agent, or Firm* — Stites & Harbison, PLLC; Juan Carlos A. Marquez, Esq

(57) ABSTRACT

A cell culture apparatus is provided in which a plurality of culture vessels can be mounted and removed in a set, which has a regulation mechanism that can fix each culture vessel in the correct position, and which enables suppression of production costs. The cell culture apparatus has one or a plurality of concave portions, and can arrange and accommodate one or a plurality of culture vessels in the concave portions. Spring-type fixing devices are provided in the depth direction and the width direction, respectively, in each concave portion. The two spring-type fixing devices press against side surfaces of the culture vessel to fix the culture vessel in the culture vessel set. At this time, by pressing against the culture vessel at two points, the position of the culture vessel at the time of fixing can be maintained with good accuracy.

11 Claims, 12 Drawing Sheets

CELL CULTURE APPARATUS AND CONTROL METHOD THEREOF

CLAIM OF PRIORITY

The present application claims priority from Japanese application JP 2006-338067 filed on Dec. 15, 2006, the content of which is hereby incorporated by reference into his application.

CROSS REFERENCE TO RELATED APPLICATIONS

U.S. patent application Ser. No. 10/767,993 (now abandoned), Ser. No. 11/192,023 (issued as U.S. Pat. No. 7,749,750), Ser. Nos. 11/774,093 and 11/756,015 (currently pending) are co-pending applications of the present application, the contents of which are incorporated herein by cross-reference.

BACKGROUND OF THE INVENTION

1. Field of the Invention

The present invention relates to a cell culture apparatus that cultures cells using a culture vessel, and a method that controls the cell culture apparatus.

2. Background Art

Conventionally, cell culture work is performed manually by skillful workers in a clean room that has been completely sterilized. Therefore, when culturing cells in large amounts in preparation for industrialization, time and expense is required to educate and train workers and the workload of the workers increases, and there is a possibility of human errors or taking of samples mistakenly and also of contamination caused by humans who possess fungi or the like. A large amount of costs are incurred to provide countermeasures for these possibilities. This represents a large barrier with respect to industrialization. These problems can be solved by automating a series of culture operations. With respect to automation of a step in cell culturing, JP Patent Publication (Kokai) No. 2006-149237 describes a case of automating a step in which a culture medium is introduced into a culture vessel such as for seeding of cells or exchanging the medium. In the method of connecting a joint and a culture vessel described in JP Patent Publication (Kokai) No. 2006-149237, a robot manipulator is used for attaching and detaching the culture vessel and the joint on the manipulator side. The configuration is such that, at that time, a connection can be made in a state in which a clean state is maintained in which a leakage of culture medium is prevented between the inside of the culture vessel and a tube of the joint through a valve by a resin membrane. Further exchange of the medium is carried out by supplying the culture medium from the bottom and discharging the medium from the top in a state in which the culture vessel that is connected by the manipulator is stood in the vertical direction.

Further, a method may be considered which makes it possible to rapidly and efficiently transfer a culture medium from a plurality of culture vessels, reduce loss of the culture medium and readily carry out washing. One example thereof is described in JP Patent Publication (Kokai) No. 2004-89126. In this case, a culture vessel is provided in which a plurality of culturing holes for introducing a culture medium are formed. Through holes that penetrate through the culture vessel and open on the outer surface side of the culture vessel are formed in the bottom of these culturing holes, and means is provided that forcibly discharges the culture medium in the culturing holes from the through holes.

SUMMARY OF THE INVENTION

Cell transplantation may involve autotransplantation in which cells that were extracted from an individual are treated in vitro and returned to the same individual or allotransplantation in which cells that were extracted from another individual such as in the case of a body donation are treated in vitro and transplanted to an individual of the same type. For autotransplantation, because it is only necessary to produce a quantity of tissue that is sufficient for treating the affected area of the relevant individual and because the amount of cells that can be extracted is also small, culturing is performed using one or a plurality of culture vessels. In contrast, for allotransplantation, since many cells that are supplied by a body donation or the like are used and that number of cells is increased in large quantities to produce a large amount of tissue, culturing is performed using many culture vessels.

However, when culture vessels are treated one at a time in a step of exchanging medium or seeding of cells in automated culturing for allotransplantation or the like, a large amount of time is required. This becomes a problem not only with respect to costs, but also with respect to quality control since the activity of the cultures or cells is not uniform and other environmental stresses also act on the cells. Therefore, to reduce the treatment time for seeding of cells or exchanging medium, a method is required that treats a plurality of culture vessels at the same time. Further, in this case it is also necessary that there are no variations with respect to the positioning of each of the plurality of culture vessels. Furthermore, when accommodating a plurality of culture vessels, since the weight increases in comparison to the case of a single culture vessel, the power of the motor of a conventional manipulator is too small. Hence, it is necessary to exchange the motor for a more powerful one, and it is not possible to suppress the cost of the cell culture apparatus by making use of a manipulator that is suited for a single culture vessel.

The present invention was made in consideration of the above circumstances, and an object of the present invention is to provide a cell culture apparatus in which a plurality of culture vessels can be mounted and taken off in a set and also has a regulation mechanism that enables each culture vessel to be fixed in the correct position. A further object of the present invention is to provide a cell culture apparatus that suppressed costs.

To solve the above described problems, according to the present invention there is provided a culture vessel set having one or a plurality of concave portions in which one or a plurality of culture vessels can be arranged and accommodated. In the concave portions of the culture vessel set, a spring-type fixing device is provided in the depth direction and the width direction, respectively. The two spring-type fixing devices press against the sides of the culture vessel to fix the culture vessel set. At this time, by being pressed at two points, it is possible to retain the position of the culture vessel with good accuracy at a time of fixing. A hole with a valve is provided on the top surface of the culture vessel for connecting to the culture space inside the culture vessel, and when a culture vessel is fixed in the culture vessel set, a culture medium can be supplied from the top surface thereof.

A cell culture apparatus is provided that comprises a manipulator having a joint that is connected with flow channels to simultaneously supply a culture medium to inside a culture vessel set in which one or a plurality of culture vessels are fixed. Tubes that are connected to the flow channels extrude from the lower portion of the joint in a joint portion of the manipulator, and those tubes connect to holes of the culture vessels to enable supply of a liquid to inside the culture vessels that are held in a vertical direction by the manipulator. The culture vessel set is sandwiched between a rack and the joint at that time, and by rotating the rack the entire structure comprising the culture vessel set, the joint, and the rack can be stood up vertically. By placing the entire structure in the horizontal direction after supplying the liquid and then detaching the joint, seeding of cells or exchange of a medium can be realized.

More specifically, a cell culture apparatus according to the present invention is an apparatus that cultures cells using culture vessels, comprising a culture vessel set having a plurality of concave portions for accommodating a plurality of culture vessels, wherein each of the plurality of concave portions have pressurization means that is disposed in at least one portion of an inner wall and that pressurizes the culture vessels that is accommodated.

Further, the cell culture apparatus according to the present invention is a cell culture apparatus that cultures cells using culture vessels, comprising: a culture vessel set that holds a plurality of culture vessels; a mounting rack for mounting the culture vessel set; a joint having at least one liquid supply means that supplies a liquid to the plurality of culture vessels and at least one liquid recovery means that discharges a liquid from the plurality of culture vessels; first coupling means that couples a liquid inlet portion of the plurality of culture vessels and the liquid supply means; second coupling means that couples a liquid outlet portion of the plurality of culture vessels and the liquid recovery means; and a manipulator for connecting the liquid supply means and the liquid recovery means to the plurality of culture vessels through the first and the second coupling means, that moves the joint and inserts the culture vessel set between the joint and the mounting rack. The cell culture apparatus further comprises state changing means that changes the culture vessel set, the joint, and the mounting rack that are integrated into one piece from a horizontal state to a vertical state, wherein the liquid supply means and the liquid recovery means operate in a vertical state. Further, the state changing means is provided in the mounting rack and comprises a first rotating shaft and a drive portion for rotating the culture vessel set, the joint, and the mounting rack that are integrated into one piece, the joint has a second rotating shaft that rotates in an integrated condition with the first rotating shaft, and the mounting rack has a bearing portion that accommodates the second rotating shaft in an integrated condition with the first rotating shaft. The first rotating shaft is provided on a center line of the mounting rack and the second rotating shaft is provided on a center line of the joint.

The present invention also provides a control method of a cell culture apparatus. In this case the cell culture apparatus comprises: a culture vessel set that holds a plurality of culture vessels; a mounting rack for mounting the culture vessel set; a joint having at least one liquid supply means that supplies a liquid to the plurality of culture vessels and at least one liquid recovery means that discharges a liquid from the plurality of culture vessels; first coupling means that couples a liquid inlet portion of the plurality of culture vessels and the liquid supply means; second coupling means that couples a liquid outlet portion of the plurality of culture vessels and the liquid recovery means; a manipulator for moving the joint, first detection means that detects that the culture vessel set is mounted in the mounting rack; and control means that controls an operation of the cell culture apparatus.

For this cell culture apparatus, the control method comprises a first step in which the control means moves the manipulator based on a detection result obtained by the detection means, inserts the culture vessel set between the joint and the mounting rack, and connects the liquid supply means and the liquid recovery means to the plurality of culture vessels through the first and the second coupling means. The cell culture apparatus further comprises second detection means that detects that the culture vessel set is inserted in an integrated condition between the joint and the mounting rack, and state changing means that changes an orientation of the culture vessel set, the joint, and the mounting rack that are integrated into one piece. For this cell culture apparatus, the control method further comprises a second step in which the control means controls the state changing means so as to place the culture vessel set, the joint, and the mounting rack that are integrated into one piece into a vertical state from a horizontal state based on a detection result of the second detection means, and a third step in which the control means causes the liquid supply means and the liquid recovery means to operate in a vertical state.

The state changing means is provided in the mounting rack and comprises a first rotating shaft and a drive portion for rotating the culture vessel set, the joint, and the mounting rack that are integrated into one piece. The joint has a second rotating shaft that rotates in an integrated condition with the first rotating shaft. The mounting rack has a bearing portion that accommodates the second rotating shaft in an integrated condition with the first rotating shaft. The detection means is configured to detect that the second rotating shaft is accommodated in the bearing portion.

Further features of the present invention will be apparent from the description of the preferred embodiments for implementing the present invention and the attached drawings as described hereunder.

According to the cell culture apparatus of the present invention, a plurality of culture vessels can be mounted and dismounted in a set, and each culture vessel can be fixed in the correct position. Further, the cost of the cell culture apparatus can be suppressed by making use of a conventional manipulator.

DETAILED DESCRIPTION OF THE PREFERRED EMBODIMENTS

Figure 1:
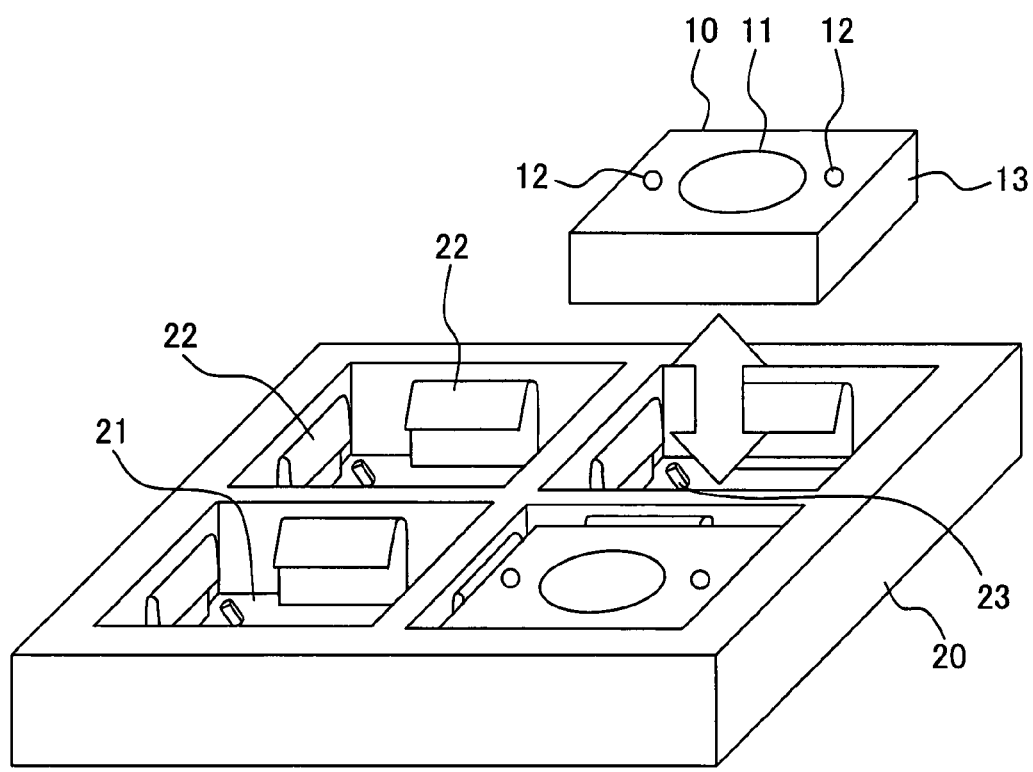
FIG. 1 is a view that illustrates an embodiment of the present invention, and shows an overall view relating to connection of a culture vessel and a culture vessel set.

Hereunder, an embodiment of the present invention is described in detail with reference to the attached drawings. However, this embodiment represents no more than one example for implementing the present invention, and it should be understood that the embodiment does not limit the present invention.

<Cell Culture Apparatus>

A feature of the cell culture apparatus that is used with the present invention is, as described later, the configuration and operation of a culture vessel 10, a culture vessel set 20, and a joint 50 that performs the supply and discharge of a liquid into and out of each culture vessel. The configuration of a conventional cell culture apparatus can be used for the remaining configuration, and therefore the remaining configuration is not shown. However, the minimum configuration of the cell culture apparatus will now be described as a precaution. The cell culture apparatus comprises a culture chamber; a culture vessel set introduction portion for introducing the culture vessel set 20 containing a plurality of the culture vessels 10 into a culture chamber and for removing it therefrom; conveying means that conveys the culture vessel set 20 between the culture vessel set introduction portion and a predetermined culturing position; and a manipulator 51 that handles the culture vessel set 20 at the predetermined culturing position.

<Culture Vessel and Culture Vessel Set>

Figure 2:
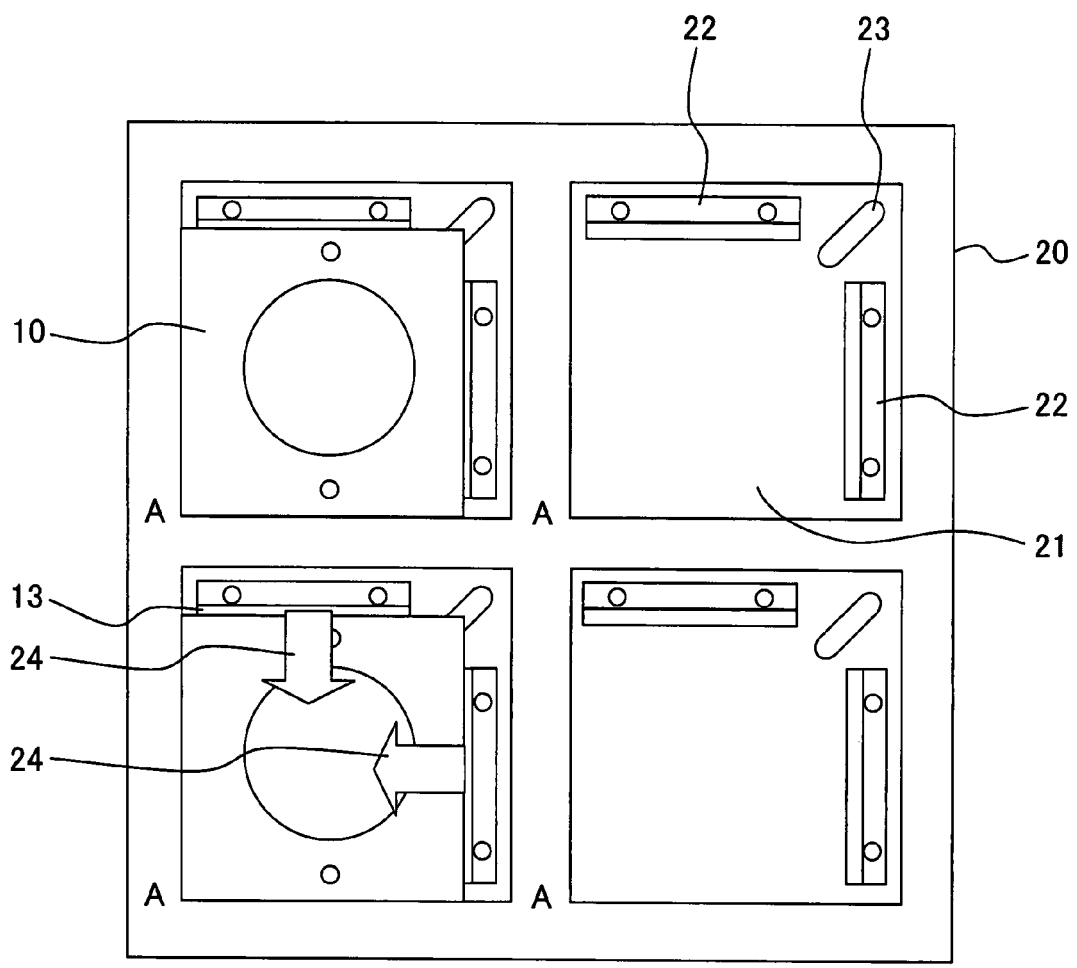
FIG. 2 is a view that illustrates an embodiment of the present invention, and shows a configuration diagram of the top surface when connecting to a culture vessel set that has one or a plurality of concave portions inside and which can fix a culture vessel by means of two spring-type fittings.
Figure 3:
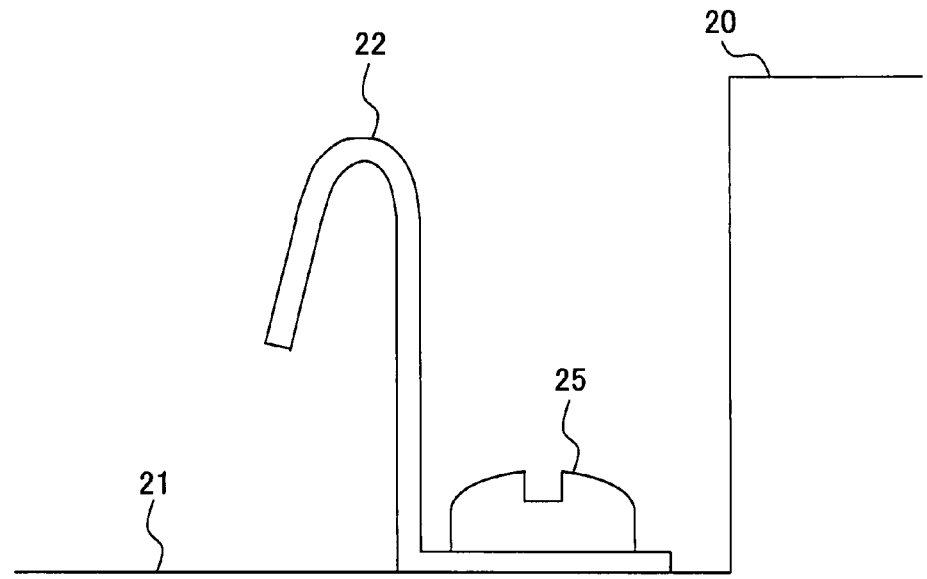
FIG. 3A is a view that illustrates the configuration of a spring-type fixing device for fixing a culture vessel.
FIG. 3B is a conceptual diagram that illustrates a method for fixing a culture vessel using a spring-type fixing device.
Figure 3:
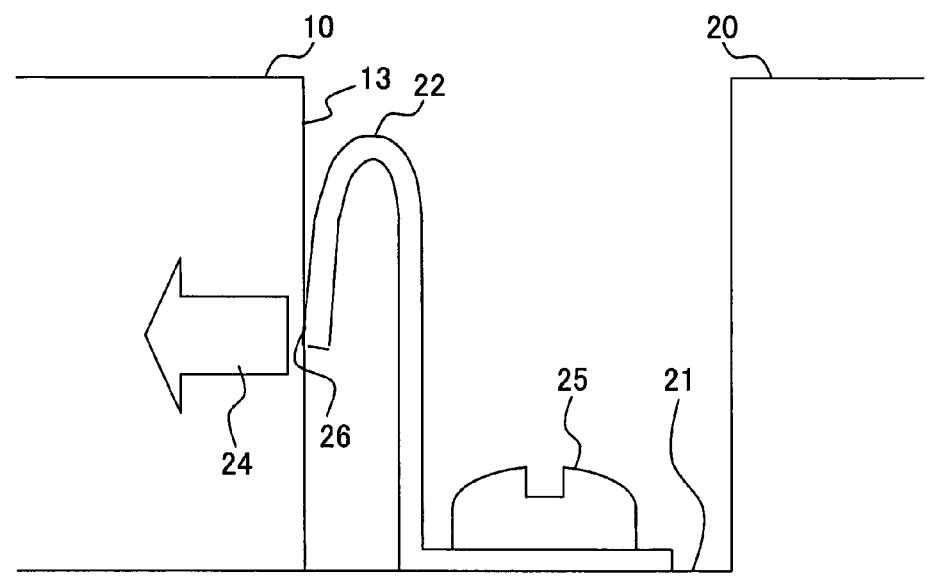
Figure 4:
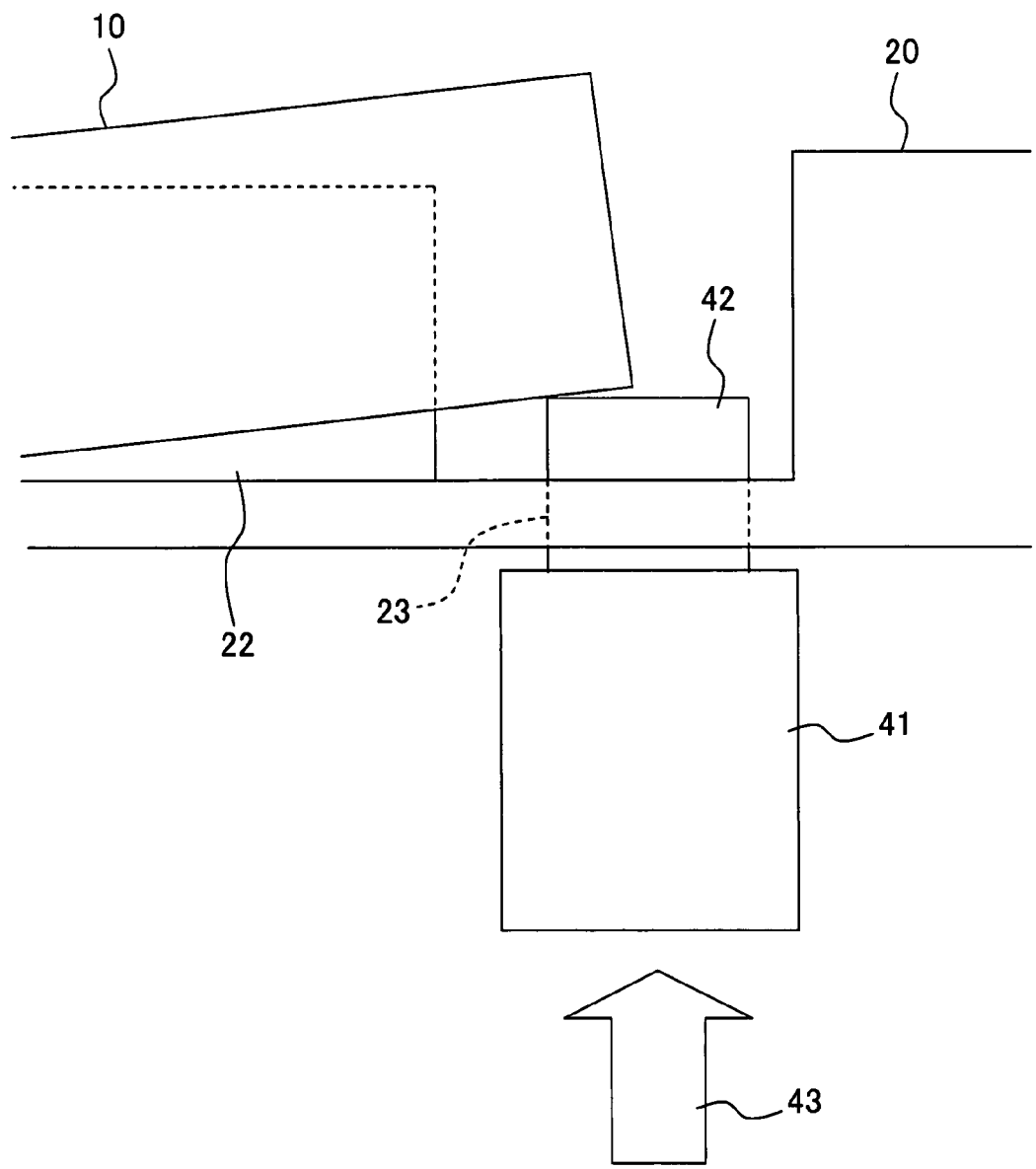
FIG. 4 is a conceptual diagram that illustrates a method for taking out a culture vessel that is fixed in the culture vessel set.

FIG. 1 is an overall view of a state when connecting the culture vessel 10 and the culture vessel set 20, which best illustrates the features of the present invention. FIG. 2 is a top view of the configuration of the culture vessel set 20. FIGS. 3A and B are schematic diagrams of a spring-type fixing device 22 when placing the culture vessel 10 in the culture vessel set 20. FIG. 4 is a schematic diagram relating to a method of taking the culture vessel 10 out from the culture vessel set 20.

The configurations of the culture vessel 10 and the culture vessel set 20 as shown in FIG. 1, FIG. 2, FIG. 3, and FIG. 4 and the connection thereof will now be described.

First, the configurations of the culture vessel 10 and the culture vessel set 20 as shown in FIG. 1 are described. The culture vessel 10 has a culture space 11 on the inside for culturing cells with a closed system. A culture medium is inserted therein to culture cells. A pair of connection holes 12 for supplying and discharging a culture medium from and to the outside are provided on the top surface of the culture vessel 10. When supplying a culture medium, the culture medium is allowed to flow from one of the connection holes 12, and the culture medium and gas is discharged from the other connection hole 12. The culture vessel set 20 has one or a plurality of concave portions 21, and the culture vessel 10 is inserted into one of the concave portions 21. At that time, two spring-type fixing devices 22 that are inside the concave portion 21 are used to fix the culture vessel 10. The spring-type fixing devices 22 press against the culture vessel side surface 13 to fix the culture vessel 10. A dismounting hole 23 for taking out the culture vessel 10 is also provided in the culture vessel set 20, and a fitting 41 can be inserted therein to take out the culture vessel 10 of interest. The dismounting hole 23 penetrates the bottom surface of the culture vessel set 20.

The configuration of the culture vessel set 20 will now be described using FIG. 2. Two spring-type fixing devices 22 and one dismounting hole 23 are provided for each concave portion 21 of the aforementioned culture vessel set 20. The spring-type fixing devices 22 are fixed to the bottom surface or the side surface of the concave portion 21 of the culture vessel set 20. The spring-type fixing devices 22 are each provided in the vertical direction, and a raw material having the strength of stainless steel is used so that the spring-type fixing devices 22 do not rust in a high humidity environment when culturing. When the culture vessel 10 is set in the concave portion 21, by the spring-type fixing devices 22 pushing the culture vessel side surfaces 13 with forces 24 from two directions, the positioning accuracy in the horizontal direction of the culture vessel 10 when setting the culture vessel 10 can be enhanced.

Further, a force is applied to all the culture vessel side surfaces 13 thereby, and it is therefore possible to prevent the culture vessel 10 from moving in the vertical direction when an external force is applied or from detaching from the culture vessel set 20. By providing two of the spring-type fixing devices 22 at side surface portions that adjoin each other in each concave portion 21 as described above, each culture vessel 10 can be positioned with good accuracy at an angle portion A (see FIG. 2) of the concave portion 21. Thus, since the culture vessel 10 is pressingly supported at four surfaces by the spring-type fixing devices 22 and the side surfaces on which the spring-type fixing devices 22 are not disposed in the concave portion 21, disposition errors (displacement) of the culture vessel 10 can be suppressed to a minimum. In this connection, the disposition positions of the two spring-type fixing devices 22 need not necessarily be the positions shown in FIG. 2, and any side surface may be used as long as the spring-type fixing devices 22 make an L-shape and are at the same positions in all of the concave portions 21.

The configuration of the spring-type fixing device 22 will now be described in more detail using FIG. 3. FIG. 3A shows the state before connecting the culture vessel 10. FIG. 3B shows the state after connecting the culture vessel 10. As shown in FIG. 3A, the spring-type fixing device 22 is strongly fixed with a screw 25 or the like to the bottom surface or side surface of the concave portion 21 of the culture vessel set 20. The screw 25 is composed of a raw material that does not rust, such as stainless steel or a resin. Further, although the spring-type fixing devices 22 are in a free state before connection of the culture vessel 10, after connecting the culture vessel 10, as shown in FIG. 3B, by pressing the culture vessel side surface 13 with the force 24 with the spring-type fixing device 22, a high positioning accuracy can be maintained in the horizontal direction as described above. Movement in the vertical direction can also be prevented by the frictional force of the pressing portion 26. More specifically, each culture vessel 10 is firmly held in each concave portion 21 of the culture vessel set 20 by the force 24 (force in a direction that is substantially parallel to the bottom surface of the concave portion 21) that is generated by a repulsive force of the spring-type fixing device 22 and a frictional force (force in a direction that is substantially perpendicular to the bottom surface of the concave portion 21) between the spring-type fixing device 22 and the culture vessel 10 that is generated at the pressing portion 26.

An operation for removing the culture vessel 10 from the culture vessel set 20 will now be described using FIG. 4. First, a tip 42 of a removal fitting 41 having a convex portion in a shape that matches a removal hole 23 of the culture vessel set 20 is inserted into the removal hole 23. Next, the inserted fitting 41 is pushed out from the bottom surface of the culture vessel set 20 towards the top surface thereof. Thus, since the culture vessel 10 is displaced from the standard position of the concave portion 21 of the culture vessel set 20, it is easy to remove the culture vessel 10. To enable sterilization, the removal fitting 41 is composed of a material that is water resistant, temperature resistant, and gas resistant.

In this connection, the removal operation may be implemented by, for example, removing the culture vessel set 20 to outside of the cell culture apparatus from the culture vessel set introduction portion, after which the operator (for example, physician or the like) inserts the removal fitting 41 into the removal hole 23 to remove a culture vessel 10 at a stage when the respective culture vessel 10 is to be used. Alternatively, the removal operation may be implemented by adopting a configuration in which a desired culture vessel is automatically disengaged from the concave portion 21 at the culture vessel set introduction portion upon an instruction from an operator.

<Configuration and Operation of Manipulator and Connection of Joint and Culture Vessel>

Figure 5:
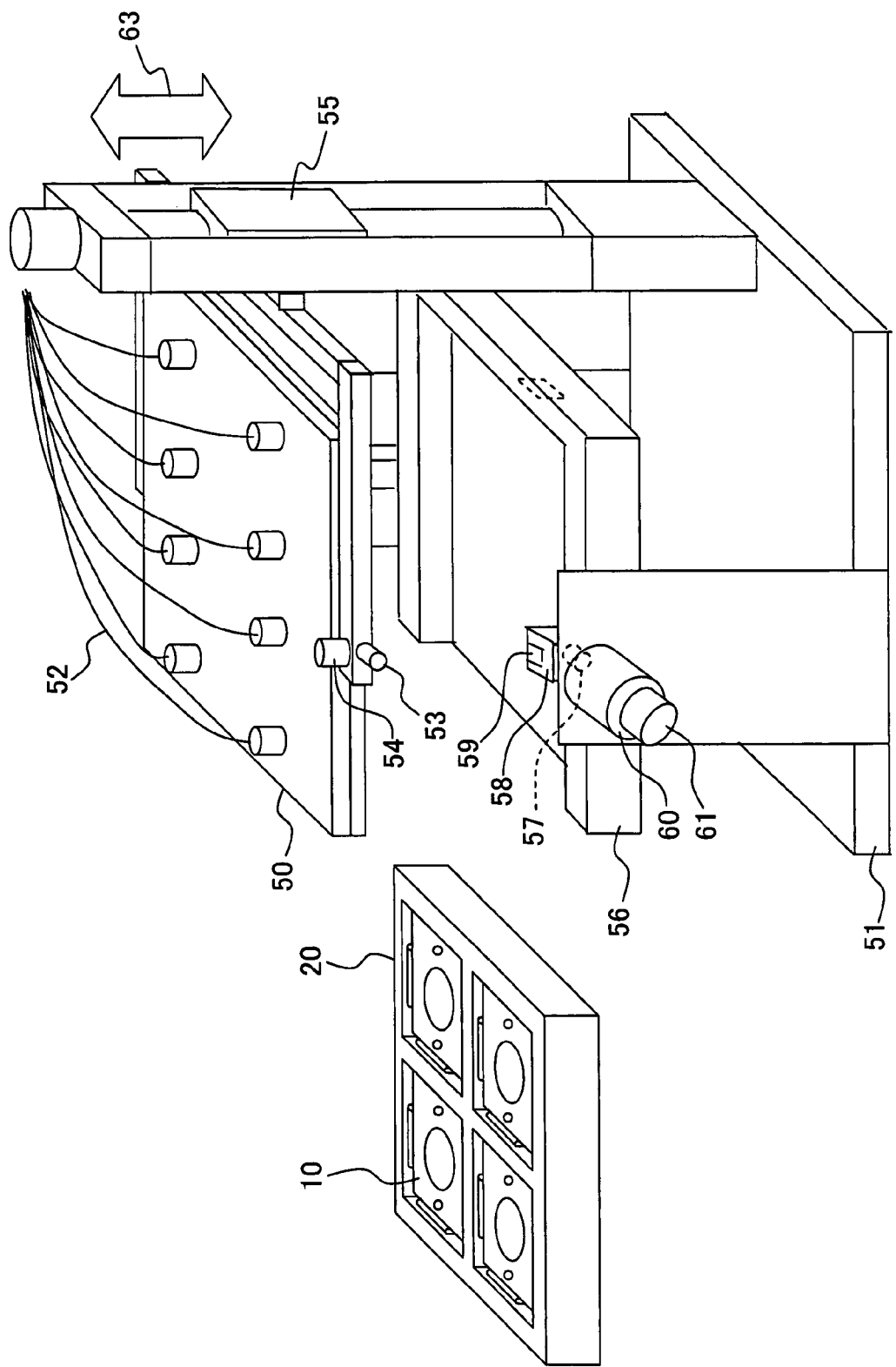
FIG. 5 is an overall configuration diagram of a manipulator that connects a joint that is connected to flow channels to a culture vessel.

FIG. 5 is a configuration diagram of a manipulator 51 having a joint 50 for connecting to the culture vessel set 20 and supplying a liquid into the culture vessel 10. FIGS. 6A to 6C are schematic diagrams that illustrate an operation that connects the culture vessel set 20 and the manipulator 51. FIGS. 7A and 7B are views that illustrate in detail an operation that connects the joint 50 and the culture vessel set 20. FIGS. 8A and 8B are schematic drawings that relate to connection of flow channels 52 of the joint 50 and the culture vessels 10.

The configuration of the manipulator 51 having the joint 50 for supplying a liquid into the culture vessel 10 of the culture vessel set 20 will now be described using FIG. 5. The manipulator 51 has a joint 50 and flow channels 52 that are connected thereto; a rotating shaft 53 for rotating the joint 50; a stopper 54 for restraining the rotating shaft 53 so that the rotating shaft 53 does not rotate; a motor 55 for causing the joint 50 to move vertically (in the direction of an arrow 63); a culture vessel set rack 56 for mounting the culture vessel set 20 thereon; a rotating shaft 57 for rotating the culture vessel set rack 56 and the joint 50; an arm (joint rotating shaft accommodating means: bearing portion) 58; and a connection groove 59 in which a rotating shaft 53 of the joint 50 is accommodated. The manipulator 51 inserts the culture vessel set 20 between the joint 50 and the culture vessel set rack 56, and rotates all of these parts together in the vertical direction from the horizontal direction by rotating the rotating shaft 57 of the culture vessel set rack 56 using the motor 60. At this time, a vertical state is detected by a sensor 61 such as an encoder, and based on the detection result an unshown control portion for controlling the entire cell culture apparatus stops the operation of the motor 60. This mechanism makes it possible to supply a culture medium to the culture vessels 10 in a vertical state.

In a state in which the rotating shaft 53 of the joint 50 is not set in the arm 58, the stopper 54 acts to retain the joint 50 in a horizontal state. When a sensor 74 detects that the rotating shaft 53 is set in the arm 58, the aforementioned control portion releases the stopper 54 to thereby enter a state in which the rotating shaft 53 can be rotated by the motor 60. The rotating direction is detected by the sensor 61. Further, when the sensor 74 detects that the rotating shaft 53 is taken out from the arm 58, the control portion causes the stopper 54 to act again on the rotating shaft 53 to retain the joint 50 in a horizontal state so that it does not wobble.

Figure 6:
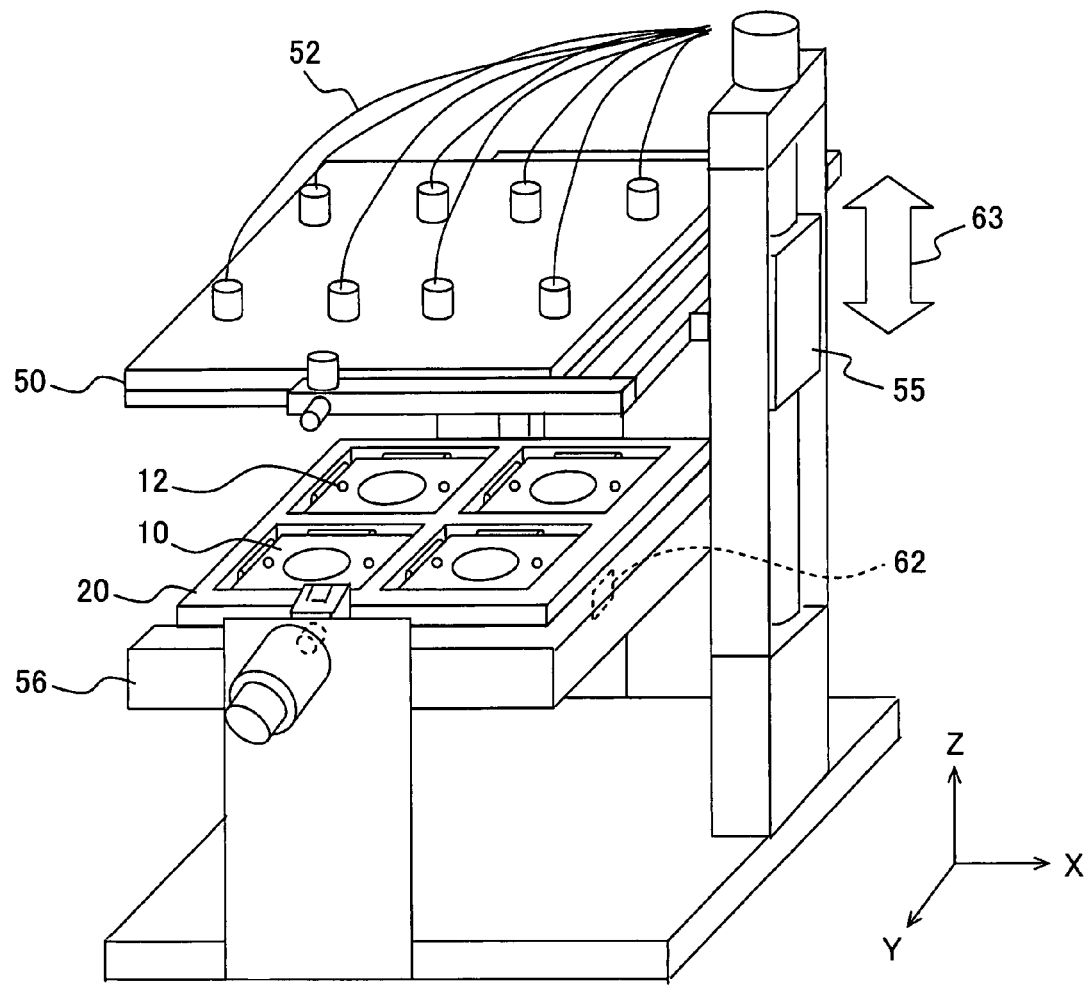
FIG. 6A is a view showing a state in which a culture vessel set is mounted on a culture vessel set rack (mounting rack)
FIG. 6B is a view showing a state in which the culture vessel set, the culture vessel set rack, and the joint are integrated into one piece.
FIG. 6C is a view showing a state in which the culture vessel set, the culture vessel set rack, and the joint that are integrated into one piece are placed in a vertical state.
Figure 6:
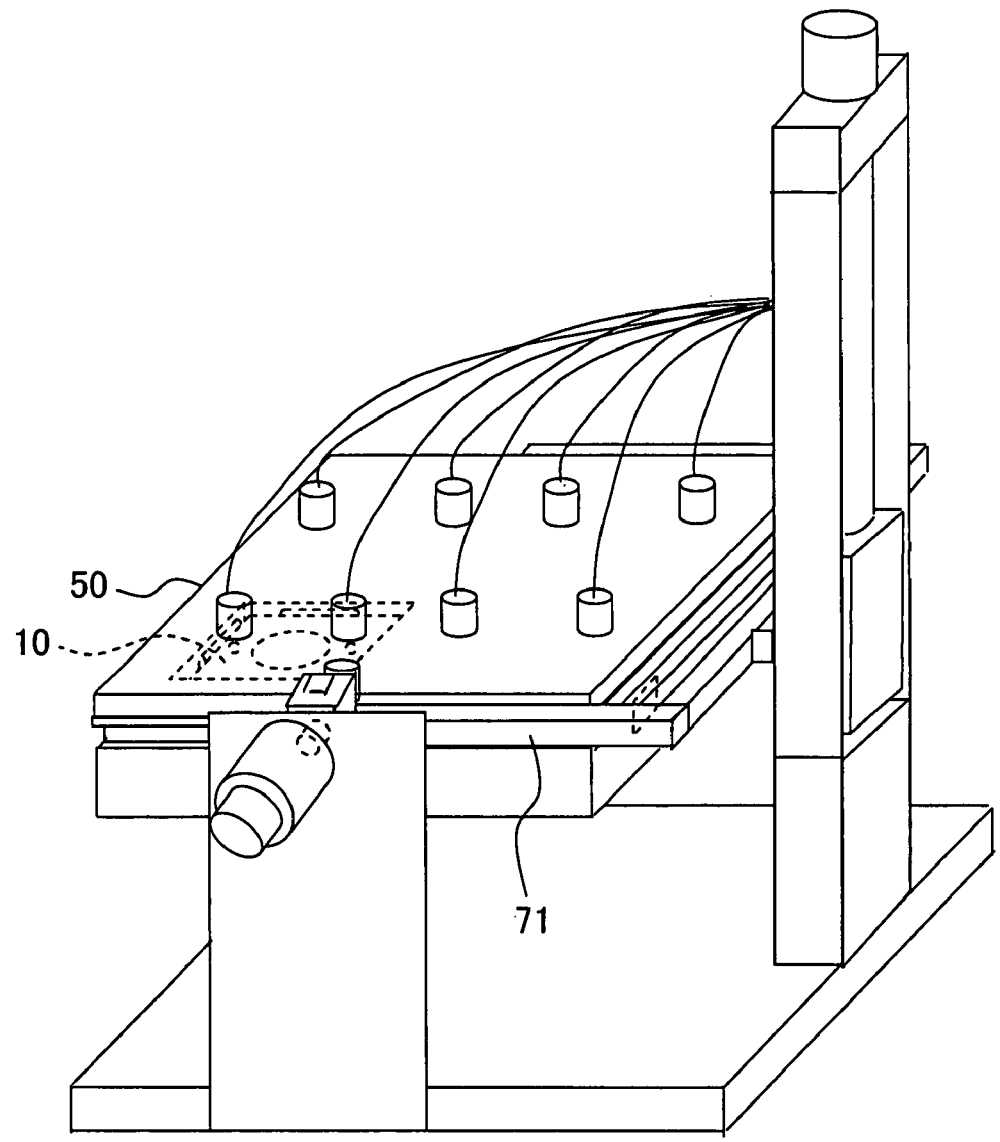
Figure 6:
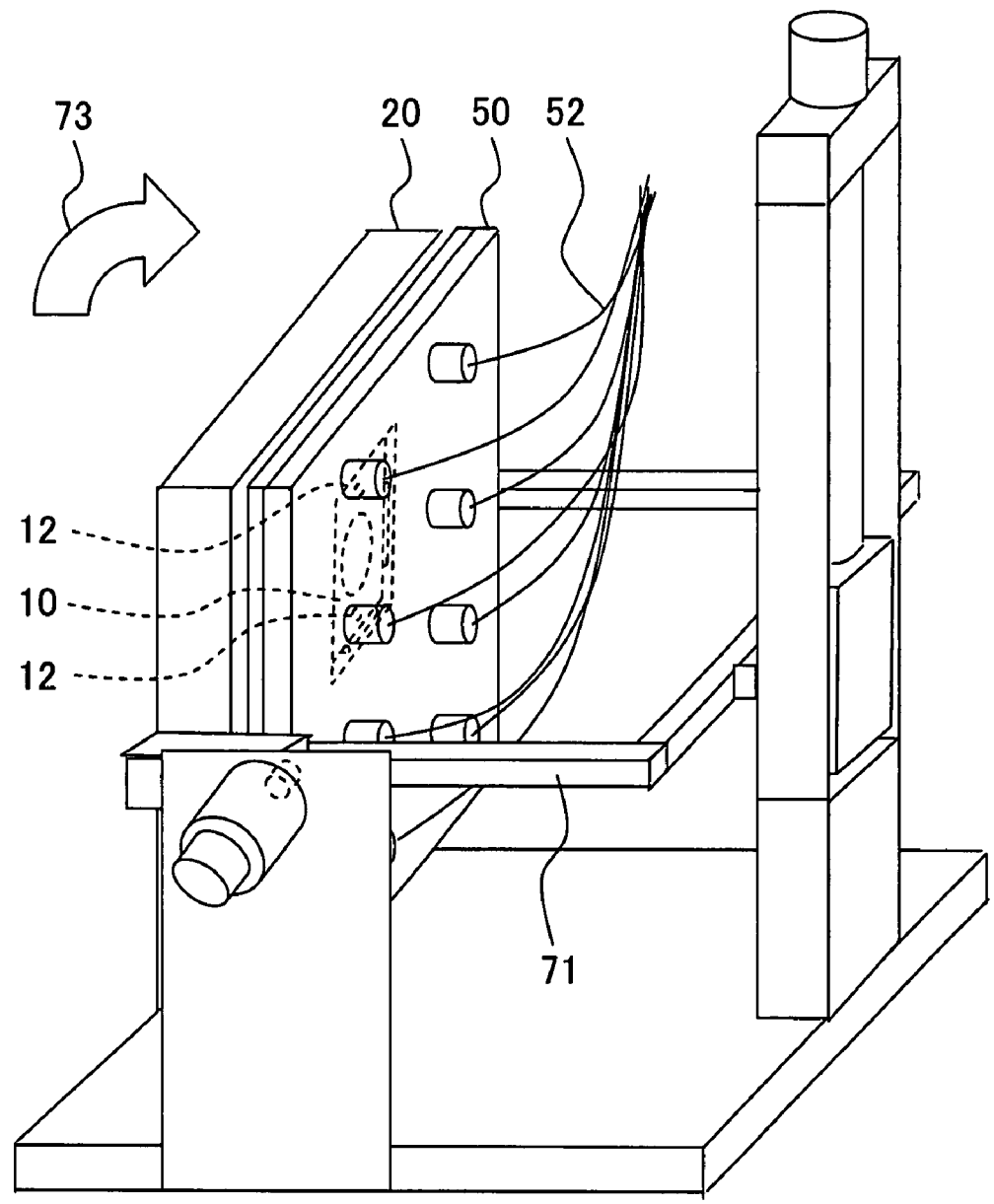

Next, connection of the culture vessel 10 and the joint 50 will be described using FIG. 6 and FIG. 7. As shown in FIG. 6A, first the culture vessel set 20 is mounted onto the culture vessel set rack 56. According to the present embodiment, the culture vessel 10 is mounted in a state in which connection holes 12 of the culture vessels 10 face the top surface and the two connection holes provided in each culture vessel 10 are parallel with the X axis. Further, the joint 50 is disposed so that the flow channels 52 come over the connection holes 12 so that they can be connected to the connection holes 12.

A sensor 62 is provided in the culture vessel set rack 56. The sensor 62 can detect that the culture vessel set 20 is mounted on the rack 56. When the sensor 62 detects that the culture vessel set 20 is mounted on the culture vessel set rack 56, the aforementioned control portion operates the motor 55 to slide the joint 50 in the vertical direction (arrow 63) and connect the connection holes 12 of the culture vessels 10 and the flow channels 52 of the joint 50. This state is shown in FIG. 6B.

Figure 7:
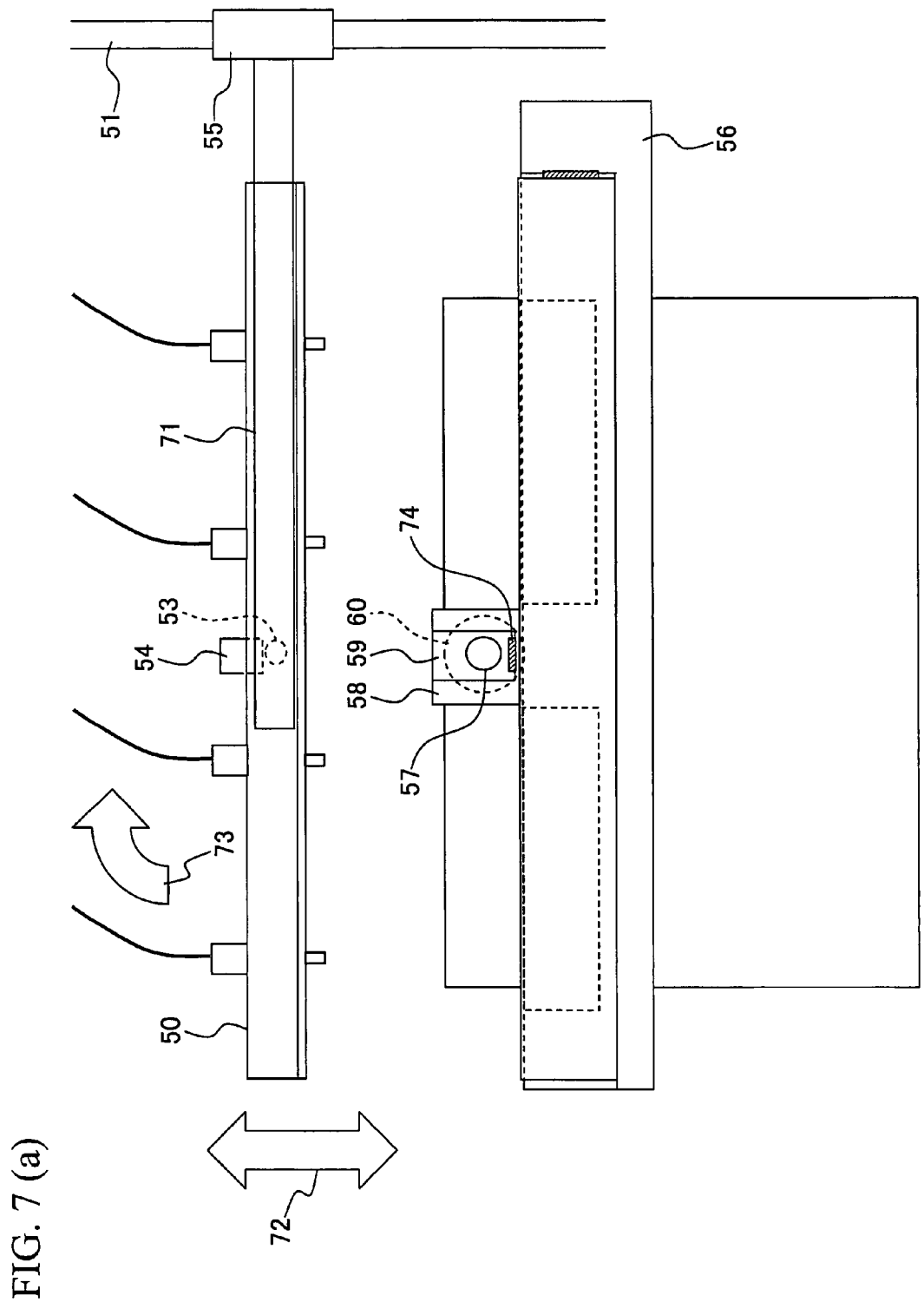
FIG. 7A is a view showing a state before the joint and the culture vessel set are connected, as viewed from the side.
FIG. 7B is a view showing a state in which the joint and the culture vessel set are connected, as viewed from the side.
Figure 7:
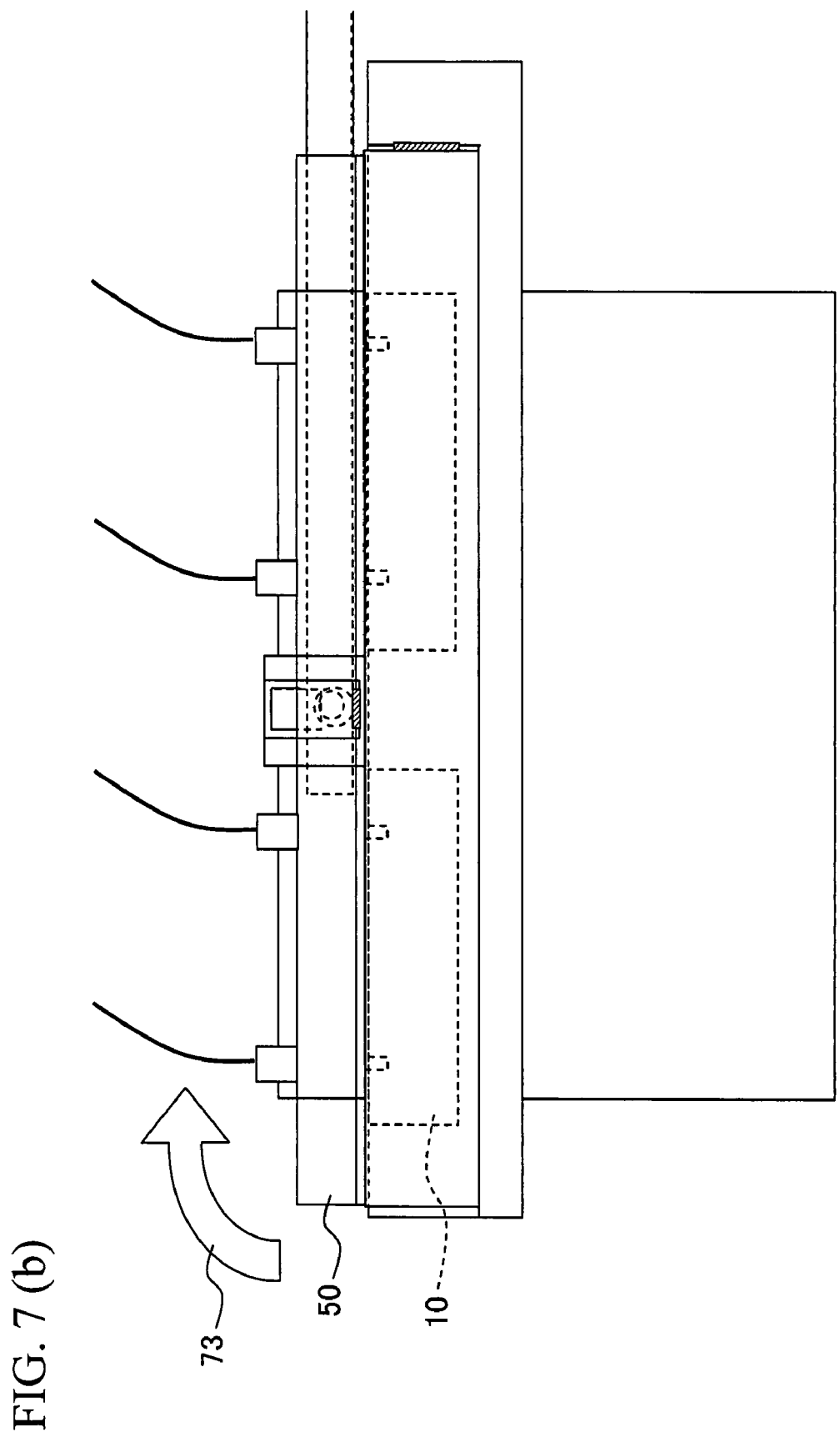

The details of the operation that connects the joint 50 and the culture vessel 10 will be now described further using FIG. 7. FIG. 7A shows the state before connection. As shown in FIG. 7A, the rotating shaft 53 is provided at substantially the center of a side surface portion of the joint 50. The rotating shaft 53 is connected to the manipulator 51 through a joint arm 71. Because the joint arm 71 is moved upward and downward by the motor 55 of the manipulator 51, the joint 50 can also move upward and downward (arrow 72). Further, the joint 50 can rotate (arrow 73) from the horizontal direction to the vertical direction by rotation of the rotating shaft 53. As described above, the stopper 54 is provided so that the joint 50 does not freely rotate, and can be fixed in a predetermined position (before connection, the position is a horizontal state).

The arm (joint rotating shaft accommodating portion) 58 is provided in the culture vessel set rack 56. The rotating shaft 57 that connects with the motor 60 is provided in the arm 58. When the rotating shaft 53 of the joint 50 is mounted in the connection groove 59 of the arm 58, the rotating shaft 57 and the rotating shaft 53 collinearly overlap.

First, when the sensor 62 detects that the culture vessel set 20 is mounted on the culture vessel set rack 56, the aforementioned control portion operates the motor 55. Subsequently, the joint 50 descends and the rotating shaft 53 of the joint 50 moves to the connection groove 59. Further, the sensor 74 inside the connection groove 59 detects that the rotating shaft 53 is inside the connection groove 59, and based on that detection result the operation of the motor 55 is stopped by the control portion. When the rotating shaft 53 of the joint 50 is accommodated in the connection groove 59 of the arm 58, as shown in FIG. 7B, the state is such that the respective rotating shafts 53 and 57 are disposed on the same line and the joint 50 and the culture vessels 10 are connected (state in which the connection holes 12 and the flow channels 52 fit together). Subsequently, when the rotating shaft 57 of the motor 60 that is connected to the arm 58 is rotated (arrow 73), the rotating shaft 53 of the joint 50 also rotates (arrow 73) in a similar manner, and the joint 50 and the culture vessels 10 can be rotated (arrow 73) in a state in which the culture vessel set 20 and the joint 50 are held in a connected state on the culture vessel set rack 56.

FIG. 6C shows a state in which the joint 50 and the culture vessels 10 are rotated (arrow 73) from the horizontal direction to the vertical direction. A culture medium is fed into the flow channels and supplied to the culture vessels 10. The configuration is such that, at this time, the culture medium is supplied from the connection holes 12 at the lower part of the culture vessel 10 and waste liquid or discharge air flows out from the connection holes 12 in the upper part of the culture vessel 10 that are paired with the connection holes 12 at the lower part thereof. After supply of the culture medium is completed, the joint 50 and the culture vessels 10 can be returned to the horizontal position to reach the state shown in FIG. 6B, the joint 50 can be detached from the culture vessels 10, and as shown in the completely separated state shown in FIG. 6A, exchange of the culture medium or filling of cells in a culture medium can be ended.

Figure 8:
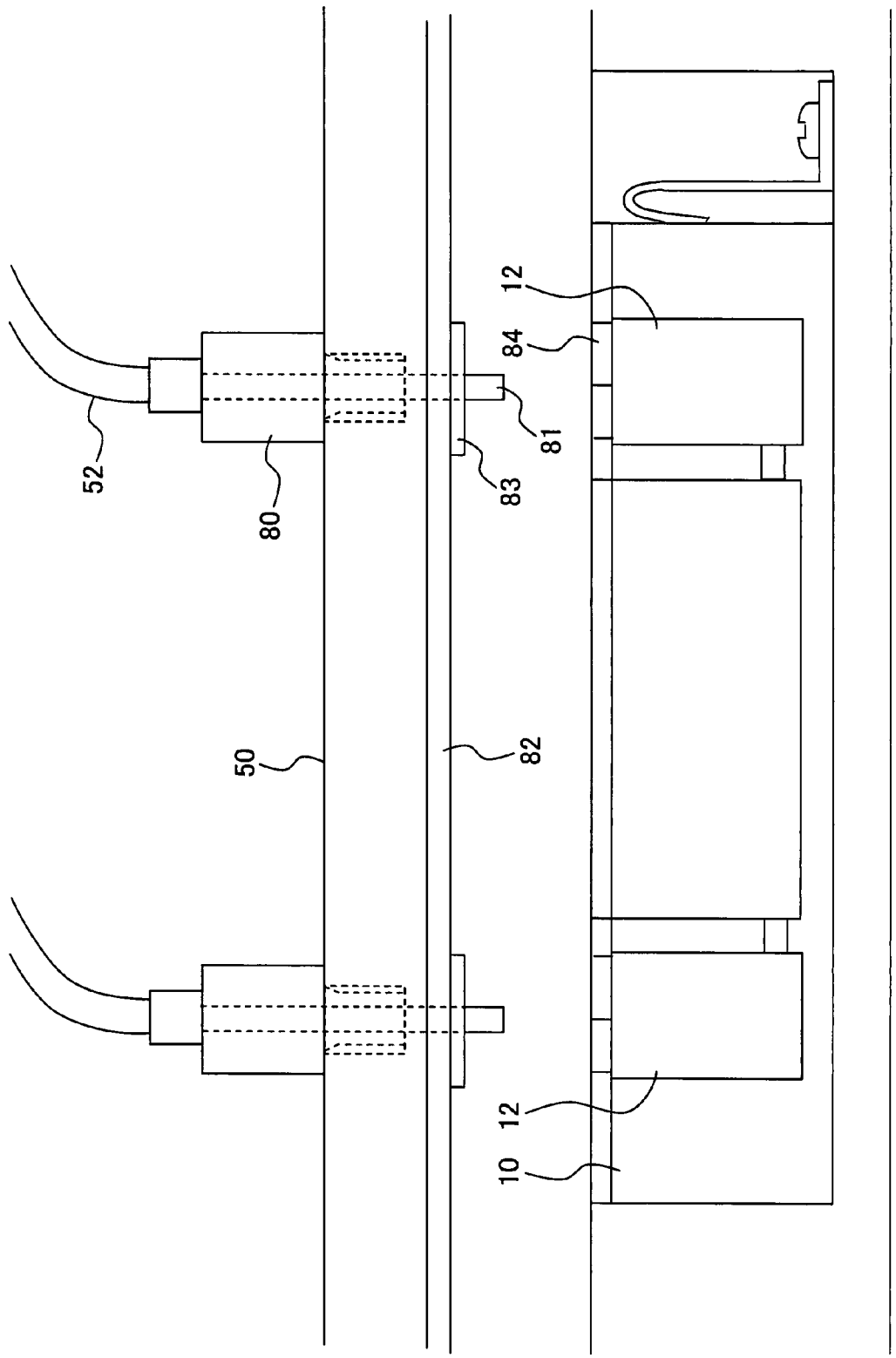
FIG. 8A is a view showing a state before one culture vessel and a flow channel of the joint are connected.
FIG. 8B is a view showing a state in which one culture vessel and a flow channel of the joint are connected.
Figure 8:
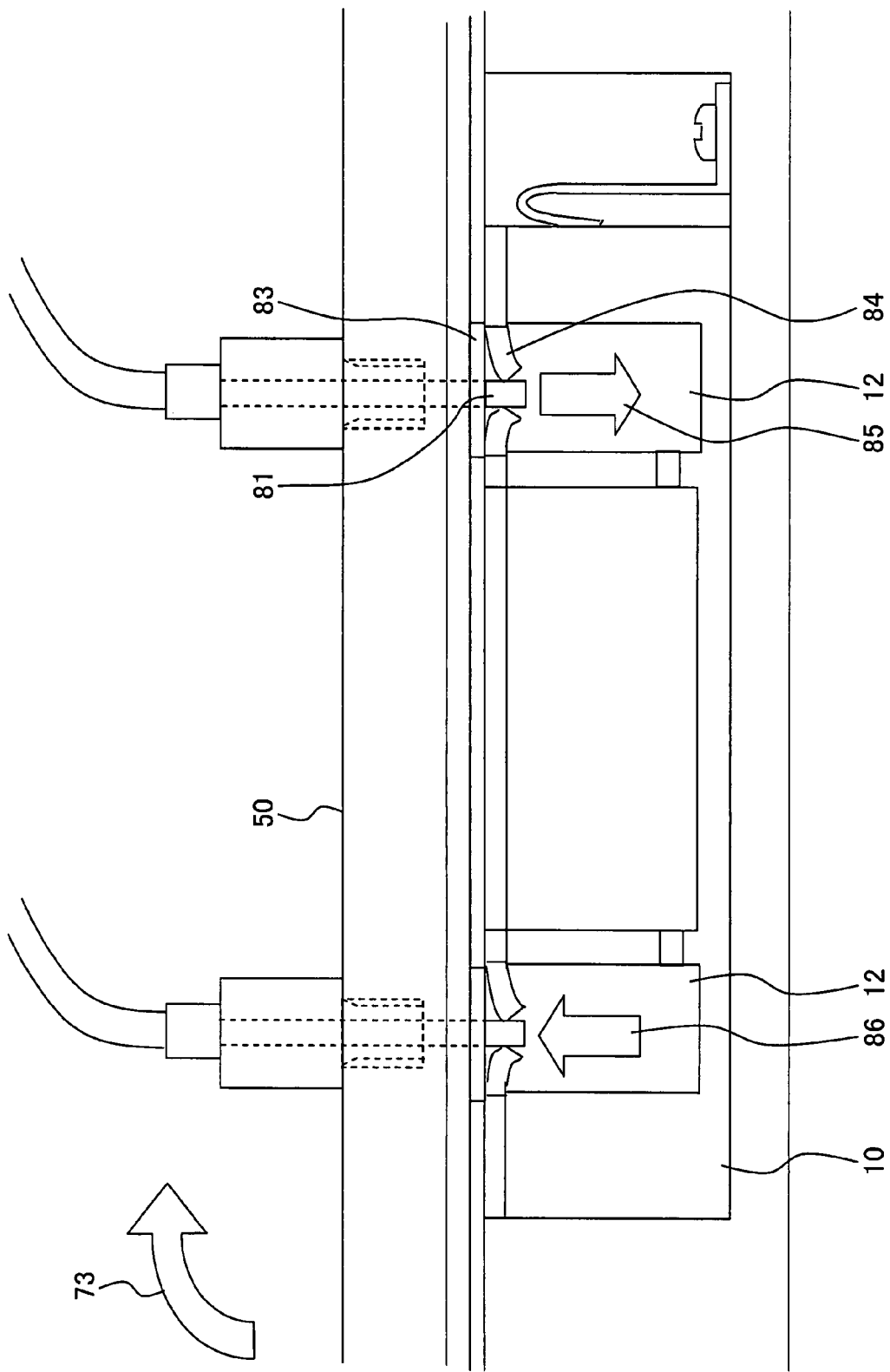

Next, the operations before and after connection of the culture vessels 10 and the flow channels 52 of the joint 50 as described above will be described in detail using FIG. 8. In FIG. 8A, a connection between the joint 50 and the flow channels 52 is made with connectors 80. A tube 81 protrudes from the tip of each connector 80. At the bottom surface of the joint 50 are provided a resin membrane (for example, silicon resin) 82 and a micro-projection 83 that is made with the same material as the resin membrane 82. Further, a resin valve 84 is affixed to the top surface of the culture vessel 10 to fulfill the role of a valve when the connection hole 12 and the tube 81 are connected.

Further, as shown in FIG. 8B, in a state in which the joint 50 and the culture vessels 10 are connected, the tube 81 is configured to push aside the resin valve 84 to connect the connection hole 12 and the flow channel 52. At this time, since the micro-projection 83 is designed to be somewhat larger than the connection hole 12, together with the action of the resin valve 84, leakage can be prevented when supplying a liquid. When a liquid is to be supplied, the joint 50, the culture vessel set 20, and the culture vessel set rack 56 that are integrated into one piece are controlled so as to rotate (arrow 73) from the horizontal direction to the vertical direction. Subsequently, at the pair of connection holes 12, a liquid 86 is supplied from below and discharge liquid and discharge air 87 are discharged from above. It is thereby possible to efficiently supply a liquid to inside of the culture vessels 10, and situations in which air bubbles are left in the culture space of the culture vessels 10 are eliminated.

After supply of the liquid is completed, the joint 50, the culture vessel set 20, and the culture vessel set rack 56 that are integrated into one piece are rotated from the vertical direction to the horizontal direction to be returned to a horizontal state. The joint 50 is then detached from the culture vessel set rack 56. Subsequently, the culture vessel set 20 and the culture vessels 10 are detached from the culture vessel set rack 56 as required.

It is thus possible to realize a highly flexible system that can supply a liquid for one or a plurality of culture vessels 10 or culture vessels 10 that are of different shapes or the like by simply changing the shape of the culture vessel set 20 and the joint 50. Further, by providing two of the spring-type fixing devices 22 for each culture vessel 10, it is possible to simply and easily enhance the positioning accuracy of the culture vessels 10 and prevent the culture vessels 10 from popping out.

<Summary>

As described above, according to the embodiment of the present invention, one or a plurality of culture vessels can be fixed by a culture vessel set while maintaining high positional accuracy. Further, a conventional manipulator can be adapted to correspond to various culture conditions by merely changing the configuration (shape) of the joint and the culture vessel set. The present cell culture apparatus can also correspond to a case in which culture vessels differ for each tissue that is the object of culturing. Since it is possible to make use of the important component parts of a conventional manipulator to realize new functions in this manner, the cost of the cell culture apparatus can be suppressed to the utmost. Furthermore, with respect to automation of cell culture work in which a high degree of cleanliness by elimination of human workers is being demanded, since the cell culture apparatus according to the above described embodiment is flexible, can support a large quantity of culture vessels, and can handle the culture vessels with high positional accuracy, it is anticipated that there will be a high demand in industries dealing with areas such as cell transplants and regenerative medicine and that the utilization possibility is high.

According to the cell culture apparatus of the present embodiment, a culture vessel set having a plurality of concave portions for accommodating a plurality of culture vessels is proposed. Each of the plurality of concave portions of the cell culture set has pressurization means (for example, comprising a plate spring) that is provided in at least one portion of an inner wall and that pressurizes the culture vessel that is accommodated therein. It is thereby possible to fix a plurality of culture vessels at set positions in the culture vessel set.

The concave portions each form a square shape having four side surfaces, and the pressurization means is disposed on two adjoining side surfaces of each concave portion. It is therefore possible to stably retain the culture vessel by means of the two pressurization means and the two side surfaces on which the pressurization means is not disposed. As described above, the pressurization means, for example, comprises a plate spring that presses against a side surface of a culture vessel, and the culture vessel is fixed by a repulsive force of the plate spring in a substantially parallel direction (lateral direction) with respect to the bottom surface and by a frictional force of the plate spring in a substantially vertical direction (longitudinal direction) with respect to the bottom surface. It is thus possible to exert a retaining force in the direction of the XY plane and also in the Z-axis direction, so that the accuracy in all directions can be maintained. Thus, since the culture vessels can be positioned at a fixed position by the pressurization means and the side surfaces of the concave portions, it is possible to improve the handling position accuracy in the manipulator.

Vessel removal holes are provided in the bottom surface of the culture vessel set. The retention force on a culture vessel can be released and the culture vessel can be removed by inserting a vessel removal member (fitting) into a vessel removal hole and pushing the vessel removal member in the upward direction. Through this removal method, a culture vessel can be easily removed even when there is a strong retention force. Further, loading a culture vessel is also simple since a spring force is utilized. It is thus possible to load the required number of culture vessels in the culture vessel set before treatment, and to remove and use only the required number of culture vessels from the culture vessel set after treatment.

Further, the cell culture apparatus according to the embodiment of the present invention comprises: a culture vessel set that holds a plurality of culture vessels; a mounting rack for mounting the culture vessel set; a joint having at least one liquid supply means that supplies a liquid to the plurality of culture vessels and at least one liquid recovery means that discharges a liquid from the plurality of culture vessels; first coupling means that couples a liquid inlet portion of the plurality of culture vessels and the liquid supply means; second coupling means that couples a liquid outlet portion of the plurality of culture vessels and the liquid recovery means; and a manipulator for moving the joint and inserting the culture vessel set between the joint and the mounting rack in an integrated condition to connect the liquid supply means and the liquid recovery means to the plurality of culture vessels through the first and the second coupling means. Since the culture vessel set is inserted between the mounting rack and the joint in this manner, it is possible to prevent leaks from the culture vessels.

The culture vessel set, the joint, and the mounting rack that are integrated into one piece are shifted from a horizontal state to a vertical state, and supply and recovery of a liquid with respect to the culture vessels is performed in that state. Since these operations are performed in a vertical state, air bubbles are not generated inside the culture vessels. Shifting of the culture vessel set, the joint, and the mounting rack from a horizontal state to a vertical state is performed by rotating with a motor. The motor is disposed in the mounting rack. A rotating shaft is also provided in the joint. The rotating shaft of the joint is fitted into a bearing that is provided in the mounting rack. The rotating shaft of the mounting rack and the rotating shaft of the joint are integrated into one piece and are rotated by the aforementioned motor, and as a result the culture vessel set, the joint, and the mounting rack that are integrated into one piece rotate and shift from a horizontal state to a vertical state. It is thus possible to simultaneously supply a culture medium to one or a plurality of culture vessels, and treatment can be performed efficiently.

In this connection, the rotating shaft of the mounting rack is provided on the center line of the mounting rack, and the rotating shaft of the joint is also provided on the center line of the joint. Thus, in comparison to a case in which the rotating shaft is at an end of a joint (see JP Patent Publication (Kokai) No. 2006-149237), since it is easier to maintain balance when shifting the culture vessel set and the joint from a horizontal state to a vertical state and it is not necessary to boost the output of the motor, a conventional manipulator for a single culture vessel can be diverted for use as a manipulator for a plurality of culture vessels. Thereby, the cost of the cell culture apparatus can be reduced.

Further, although the joint is in a horizontal state when it is not integrated as one piece with the mounting rack and the culture vessel set, a stopper that immobilizes the joint is provided to maintain that state. This stopper is not released unless the joint is integrated as one piece with the mounting rack and the culture vessel set (unless the rotating shaft of the joint is fitted into the bearing of the mounting rack). Accordingly, a connection tip portion of flow channels that form liquid supply/recovery means can be firmly connected to a liquid inlet/outlet portion of a culture vessel.

What is claimed is:

1. A cell culture apparatus that cultures cells using culture vessels, comprising:
   a culture vessel set that holds a plurality of culture vessels, the culture vessel set comprising a plurality of complementary portions receiving a respective one of the plurality of culture vessels,
   at least one first plate spring disposed in one of the complementary portions, the first plate spring having a bendable shape comprising a first arm and a second arm, the second arm having a middle portion and an end portion at an end opposite the first arm, the first arm operatively attached to one portion of an inner wall of the respective complementary portion, the middle portion and the end portion in contact with a side of a respective culture vessel,
   wherein the middle portion generates a repulsive force in a direction biasing the respective culture vessel against another portion of the inner wall facing opposite the one portion of the inner wall, and wherein the end portion engages the culture vessel, thereby generating a friction force between the culture vessel and the inner wall and the plate spring, in a direction perpendicular to the repulsive force;
   a mounting rack for mounting the culture vessel set;
   a joint having at least one liquid supply means that supplies a liquid to the plurality of culture vessels and at least one liquid recovery means that discharges a liquid from the plurality of culture vessels, wherein the liquid supply means and the liquid recovery means operate in the vertical state;
   a liquid inlet portion associated with the plurality of culture vessels, the liquid inlet portion connectable to the liquid supply means;
   a liquid outlet portion associated with the plurality of culture vessels, the liquid outlet portion connectable to the liquid recovery means;
   a manipulator for moving the joint and inserting the culture vessel set between the joint and the mounting rack to connect the liquid supply means and the liquid recovery means to the plurality of culture vessels; and
   state changing means that places the culture vessel set, the joint, and the mounting rack that are integrated into one piece in a vertical state from a horizontal state.

2. The cell culture apparatus according to claim 1, wherein:
   the state changing means is provided in the mounting rack and comprises a first rotating shaft and a drive portion for rotating the culture vessel set, the joint, and the mounting rack that are integrated into one piece;
   the joint has a second rotating shaft that rotates in an integrated condition with the first rotating shaft; and
   the mounting rack has a bearing portion that accommodates the second rotating shaft and integrates the second rotating shaft with the first rotating shaft.

3. The cell culture apparatus according to claim 2, wherein:
   the first rotating shaft is provided on a center line of the mounting rack; and
   the second rotating shaft is provided on a center line of the joint.

4. The cell culture apparatus according to claim 3, further comprising a stopper that immobilizes the joint when the joint is not integrated into one piece with the mounting rack and the culture vessel set.

5. The cell culture apparatus according to claim 2, wherein:
   the plurality of complementary portions comprise concave portions.

6. The cell culture apparatus according to claim 5, wherein:
   the concave portion forms a square shape having four side surfaces, and
   the plate spring is provided on two adjoining side surfaces.

7. The cell culture apparatus according to claim 6, wherein the plate spring presses against a side surface of the culture vessel, and the culture vessel is retained by a repulsive force of the plate spring in a substantially parallel direction with respect to the bottom surface and by a frictional force of the plate spring in a substantially vertical direction with respect to the bottom surface.

8. The cell culture apparatus according to claim 1, wherein vessel removal holes are provided in the bottom surface of the culture vessel set, and a retention force on the culture vessel can be released and the culture vessel can be removed by inserting a vessel removal member into the vessel removal hole and pushing the vessel removal member in the upward direction.

9. A control method of a cell culture apparatus that cultures cells using culture vessels, wherein the cell culture apparatus comprises:
- a culture vessel set that holds a plurality of culture vessels, the culture vessel set comprising a plurality of complementary portions receiving a respective one of the plurality of culture vessels,
- at least one first plate spring disposed in one of the complementary portions, the first plate spring having a bendable shape comprising a first arm and a second arm, the second arm having a middle portion and an end portion at an end opposite the first arm, the first arm operatively attached to one portion of an inner wall of the respective complementary portion the middle portion and the end portion in contact with a side of a respective culture vessel,
- wherein the middle portion generates a repulsive force in a direction biasing the respective culture vessel against another portion of the inner wall facing opposite the one portion of the inner wall, and wherein the end portion engages the culture vessel, thereby generating a friction force between the culture vessel and the inner wall and the plate spring, in a direction perpendicular to the repulsive force;
- a mounting rack for mounting the culture vessel set;
- a joint having at least one liquid supply means that supplies a liquid to the plurality of culture vessels and at least one liquid recovery means that discharges a liquid from the plurality of culture vessels, wherein the liquid supply means and the liquid recovery means operate in the vertical state;
- a liquid inlet portion associated with the plurality of culture vessels, the liquid inlet portion connectable to the liquid supply means;
- a liquid outlet portion associated with the plurality of culture vessels, the liquid outlet portion connectable to the liquid recovery means;
- a manipulator for moving the joint and inserting the culture vessel set between the joint and the mounting rack to connect the liquid supply means and the liquid recovery means to the plurality of culture vessels;
- a first coupling means that couples the liquid inlet portion of the plurality of culture vessels and the liquid supply means;
- a second coupling means that couples the liquid outlet portion of the plurality of culture vessels and the liquid recovery means;
- a state changing means that places the culture vessel set, the joint, and the mounting rack that are integrated into one piece in a vertical state from a horizontal state;
- a first detection means that detects that the culture vessel set is mounted on the mounting rack; and
- a control means that controls operations of the cell culture apparatus;

wherein the control method comprises:
- a first step in which the control means moves the manipulator based on a detection result generated by the first detection means, inserts the culture vessel set between the joint and the mounting rack, and connects the liquid supply means and the liquid recovery means to the plurality of culture vessels through the first and the second coupling means.

10. The control method according to claim 9, wherein:
the cell culture apparatus further comprises second detection means that detects that the culture vessel set is inserted in an integrated condition between the joint and the mounting rack, and state changing means that changes an orientation of the culture vessel set, the joint, and the mounting rack that are integrated into one piece; and the control method further comprises:
- a second step in which the control means controls the state changing means so as to place the culture vessel set, the joint, and the mounting rack that are integrated into one piece into a vertical state from a horizontal state based on a detection result of the second detection means; and
- a third step in which the control means causes the liquid supply means and the liquid recovery means to operate in the vertical state.

11. The control method according to claim 10, wherein:
the state changing means is provided in the mounting rack and comprises a first rotating shaft and a drive portion for rotating the culture vessel set, the joint, and the mounting rack that are integrated into one piece;
the joint has a second rotating shaft that rotates in an integrated condition with the first rotating shaft;
the mounting rack has a bearing portion that accommodates the second rotating shaft and integrates the second rotating shaft with the first rotating shaft; and
the detection means detects that the second rotating shaft is accommodated in the bearing portion.

* * * * *